(12) United States Patent
Chakravarty et al.

(10) Patent No.: US 10,463,584 B2
(45) Date of Patent: Nov. 5, 2019

(54) STABLE FOAM COMPOSITIONS AND METHODS OF USING THE SAME TO PROVIDE ENHANCED SENSORY AND VISUAL BENEFITS TO SKIN

(71) Applicant: The Procter & Gamble Company, Cincinnati, OH (US)

(72) Inventors: Sudeep Nmn Chakravarty, Singapore (SG); Jayant Eknath Khanolkar, Singapore (SG); Jorge Max Sunkel, West Chester, OH (US); Monalisha Nmn Paul, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 103 days.

(21) Appl. No.: 15/705,735

(22) Filed: Sep. 15, 2017

(65) Prior Publication Data

US 2018/0085293 A1 Mar. 29, 2018

Related U.S. Application Data

(60) Provisional application No. 62/398,588, filed on Sep. 23, 2016.

(51) Int. Cl.
| | |
|---|---|
| *A61K 8/04* | (2006.01) |
| *A61K 8/25* | (2006.01) |
| *A61K 8/19* | (2006.01) |
| *A61K 8/34* | (2006.01) |
| *A61K 8/41* | (2006.01) |
| *A61K 8/46* | (2006.01) |
| *A61Q 19/00* | (2006.01) |

(52) U.S. Cl.
CPC ............... *A61K 8/25* (2013.01); *A61K 8/046* (2013.01); *A61K 8/19* (2013.01); *A61K 8/342* (2013.01); *A61K 8/416* (2013.01); *A61K 8/463* (2013.01); *A61Q 19/008* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 1,985,424 | A | 12/1934 | Piggott |
| 2,703,798 | A | 3/1955 | Schwartz |
| 2,965,576 | A | 12/1960 | Wilson |
| 3,155,591 | A | 11/1964 | Hilfer |
| 3,773,064 | A | 11/1973 | Focht |
| 3,929,678 | A | 12/1975 | Laughlin et al. |
| 3,959,461 | A | 5/1976 | Bailey et al. |
| 4,275,055 | A | 6/1981 | Nachtigal et al. |
| 4,387,090 | A | 6/1983 | Bolich, Jr. |
| 5,487,884 | A | 1/1996 | Bissett et al. |
| 5,652,228 | A | 7/1997 | Bissett |
| 5,681,852 | A | 10/1997 | Bissett |
| 5,975,378 | A | 11/1999 | Bayer |
| 6,242,092 | B1 | 6/2001 | Katsuyama |
| 6,394,321 | B1 | 5/2002 | Bayer |
| 8,444,716 | B1 | 5/2013 | Felts |
| 8,470,305 | B2 | 6/2013 | Johnson et al. |
| 8,580,725 | B2 | 11/2013 | Kuhlman et al. |
| 8,936,798 | B2 | 1/2015 | Kitko et al. |
| 2003/0049212 | A1 | 3/2003 | Robinson et al. |
| 2003/0053961 | A1 | 3/2003 | Eccard |
| 2003/0215415 | A1 | 11/2003 | Mitsumatsu |
| 2003/0235597 | A1 | 12/2003 | Withiam |
| 2012/0009285 | A1 | 1/2012 | Wei et al. |
| 2012/0288465 | A1 | 11/2012 | Loechel |
| 2013/0243836 | A1 | 9/2013 | Tanner et al. |
| 2018/0085294 | A1 | 3/2018 | Sunkel |

FOREIGN PATENT DOCUMENTS

| | | | |
|---|---|---|---|
| DE | 10015148 A1 | 2/2002 | |
| DE | 102005014305 A1 | 10/2006 | |
| EP | 1752128 A1 | 2/2007 | |
| GB | 809060 A | 2/1959 | |
| JP | H08253409 A | 10/1996 | |
| JP | 3616154 B2 * | 2/2005 | |
| WO | WO2006083584 | 8/2006 | |
| WO | WO07047598 A1 | 4/2007 | |
| WO | WO2007046052 | 4/2007 | |
| WO | WO2009155264 | 12/2009 | |
| WO | WO2009155265 | 12/2009 | |
| WO | WO2010060131 A1 | 6/2010 | |
| WO | WO2013057066 A2 | 4/2013 | |
| WO | WO2013142472 A2 | 9/2013 | |
| WO | WO-2013190079 A1 * | 12/2013 | ............... A61K 8/25 |
| WO | WO-2016153946 A1 * | 9/2016 | ............ A61K 8/416 |
| WO | WO2016153946 A1 | 9/2016 | |

OTHER PUBLICATIONS

All Office Actions, U.S. Appl. No. 15/705,679.
Anonymous, Hydrocarbon—Wikipedia, Sep. 20, 2017, 8 pagesRetrieved from the internet on Oct. 19, 2017: URL:https://en.wikipedia.org/wiki/Hydrocarbon.
International Search Report and Written Opinion of the International Searching Authority, PCT/US2017/051717, dated Jan. 22, 2018, 18 pages.
International Search Report and Written Opinion of the International Searching Authority, PCT/US2017/051718, dated Nov. 15, 2017, 14 pages.

* cited by examiner

*Primary Examiner* — Susan T Tran
(74) *Attorney, Agent, or Firm* — John G. Powell

(57) ABSTRACT

A liquid foamable composition includes a cationic surfactant, a nonionic surfactant, or mixtures of these surfactants, a fatty alcohol, a sebum absorbing component. The sebum absorbing component includes silica silylate, hydrophobically or hydrophilically surface modified silica silylate or a mixture thereof. A foam composition, an aerosol product, and methods for improving sensory benefits to skin are also provided.

8 Claims, 3 Drawing Sheets

STABLE FOAM COMPOSITIONS AND METHODS OF USING THE SAME TO PROVIDE ENHANCED SENSORY AND VISUAL BENEFITS TO SKIN

TECHNICAL FIELD

The present disclosure relates generally to stable foam compositions comprising sebum absorbing powders that provide visual benefits when applied to skin, whilst providing an enhanced sensory perception during application of the foam.

BACKGROUND

There are many types of skin care products that are commercially available or otherwise known in the art, and there are many factors that can contribute to the purchase intent of a consumer when looking for such products. Critical among these factors are the sensory and visual benefits that a skin care product can provide. As such, there is a continuous desire to develop new ways to deliver a positive sensory experience to consumers.

Skin care products have often employed polymers as a way to manage rheological properties to promote performance benefits. However, use of polymers may have a negative effect on sensory benefits. For example, elevated polymer concentrations, relative to evaporating fluids, can thicken fluids that remain on the skin during product application and subsequent dry-down, resulting in tack, drag, stickiness, or other negative sensory aspects.

Using a foam composition is one way to reduce or eliminate the use of polymers. For example, foams can use air to thicken a product in place of polymers. Thus, foams can convey a desired rich and creamy aesthetic while reducing or eliminating the negative sensory aspects associated with the use of polymers. Further, foams can easily absorb into the skin as they can rapidly break down into fluids. However, certain foam compositions can lack the stability that may otherwise be provided by skin care products with polymers, resulting in a negative sensory experience for a consumer. Furthermore, some ingredients that provide visual skin care benefits, such as sebum absorbing powders, are known to be defoamers and thus, historically have not been widely used in foam form.

It is thus an object of the present invention to provide a skin care product in the form of a foam composition, which possesses robust stability and comprises sebum absorbing powders that provide acute visual benefits when applied to skin.

SUMMARY

In accordance with one example, a liquid foamable composition includes from about 0.05% to about 5%, by weight of the composition, of a cationic surfactant, 0.1% to 10%, by weight of the composition, of a fatty alcohol, and 0.1% to 10%, by weight of the composition, of a sebum absorbing powder.

The present inventors have surprisingly discovered that when sebum absorbing powder, a known defoamer, is incorporated in a composition with a percentage of cationic surfactant and fatty alcohol, the resulting foamable composition remains stable, while providing the desired sensory and visual benefits when applied to skin. Without being bound by theory, it is thought that the combination of fatty alcohol and cationic surfactant provides a composition that easily foams and that remains stable in foam form by creating a lamellar gel network. The sebum absorbing particles provide acute visual benefits on skin by controlling shine caused by generation of sebum.

In an embodiment, the foamable composition comprises a combination of cationic and nonionic surfactants. Nonionic surfactants alone may be used to provide foamable compositions. However, compared with cationic surfactants alone or a combination of cationic and nonionic surfactants, when used alone, a greater percentage of nonionic surfactant is used to generate a foam that can remain stable even at high temperatures. However, as the concentration of surfactant is increased, the liquid foamable composition becomes increasingly thick and foaming becomes more difficult. Cationic surfactants are known to cause irritation at high concentrations. Thus, while cationic surfactants may be used alone in the present invention, using a combination of nonionic surfactant with cationic surfactants permits an overall higher concentration of surfactant without causing side effects, such as irritation.

Preferably, the sebum absorbing powders includes silica, hydrated silica powders, silica silylate, hydrophobically or hydrophilically surface modified silica silylate or a mixture thereof. These sebum absorbing powders are known to provide acute skin care benefits by controlling the oily shine appearance caused by sebum secretion. Some sebum absorption powders also provide soft focus efficacy by maximizing total transmission and diffused transmission and minimizing total reflectance from the surface when applied on skin.

In accordance with another example, a foam composition is formed from combining a liquid foamable composition with a propellant. The liquid foamable composition includes from about 0.05% to about 5%, by weight of the composition, of a cationic surfactant, 0.1% to 10%, by weight of the composition, of a fatty alcohol, and 0.1% to 10%, by weight of the composition, of a sebum absorbing powder. In embodiments, the foam composition exhibits a foam density of about 0.1 g/mL to about 0.5 g/mL and is stable for up to 20 minutes with a haze value of between 20 and 90. Preferably, the initial liquid composition typically has a density of from about 0.9 g/mL to about 1.1 g/mL, and the density decreases as the liquid turns to foam.

In accordance with yet another example, an aerosol product includes a liquid foamable composition, a propellant, and a package. The liquid foamable composition includes from about 0.05% to about 5%, by weight of the composition, of a cationic surfactant, 0.1% to 10%, by weight of the composition, of a fatty alcohol, and 0.1% to 5%, by weight of the composition, of a sebum absorbing powder. In embodiments, the foam composition exhibits a foam density of about 0.1 g/mL to about 0.5 g/mL and is stable for up to 20 minutes with a haze value of between 20 and 90. Preferably, the initial liquid composition typically has a density of from about 0.9 g/mL to about 1.1 g/mL, and the density decreases as the liquid turns to foam. The package houses the liquid foamable composition and the propellant. The liquid foamable composition and the propellant are dispensable from the package as a foam, wherein such foam exhibits a foam density of about 0.1 g/mL to about 0.5 g/mL.

In accordance with still another example, a method for improving acute look benefits to skin includes applying a foam composition to the skin of a user. The foam composition includes a liquid foamable composition and a propellant. The liquid foamable composition includes from about 0.05% to about 5%, by weight of the composition, of a cationic surfactant, 0.1% to 10%, by weight of the composition, of a fatty alcohol, and 0.1% to 5%, by weight of the composition, of a sebum absorbing powder.

In an embodiment, the liquid foamable composition of the cosmetic composition, the aerosol product or the method of applying the foam comprises a surfactant comprising at least 0.05% of a cationic surfactant and a nonionic surfactant. Preferably, the ratio of cationic surfactant to nonionic surfactant is from 5:1 to 3:2.

DETAILED DESCRIPTION

I. Definitions

Figure 1:
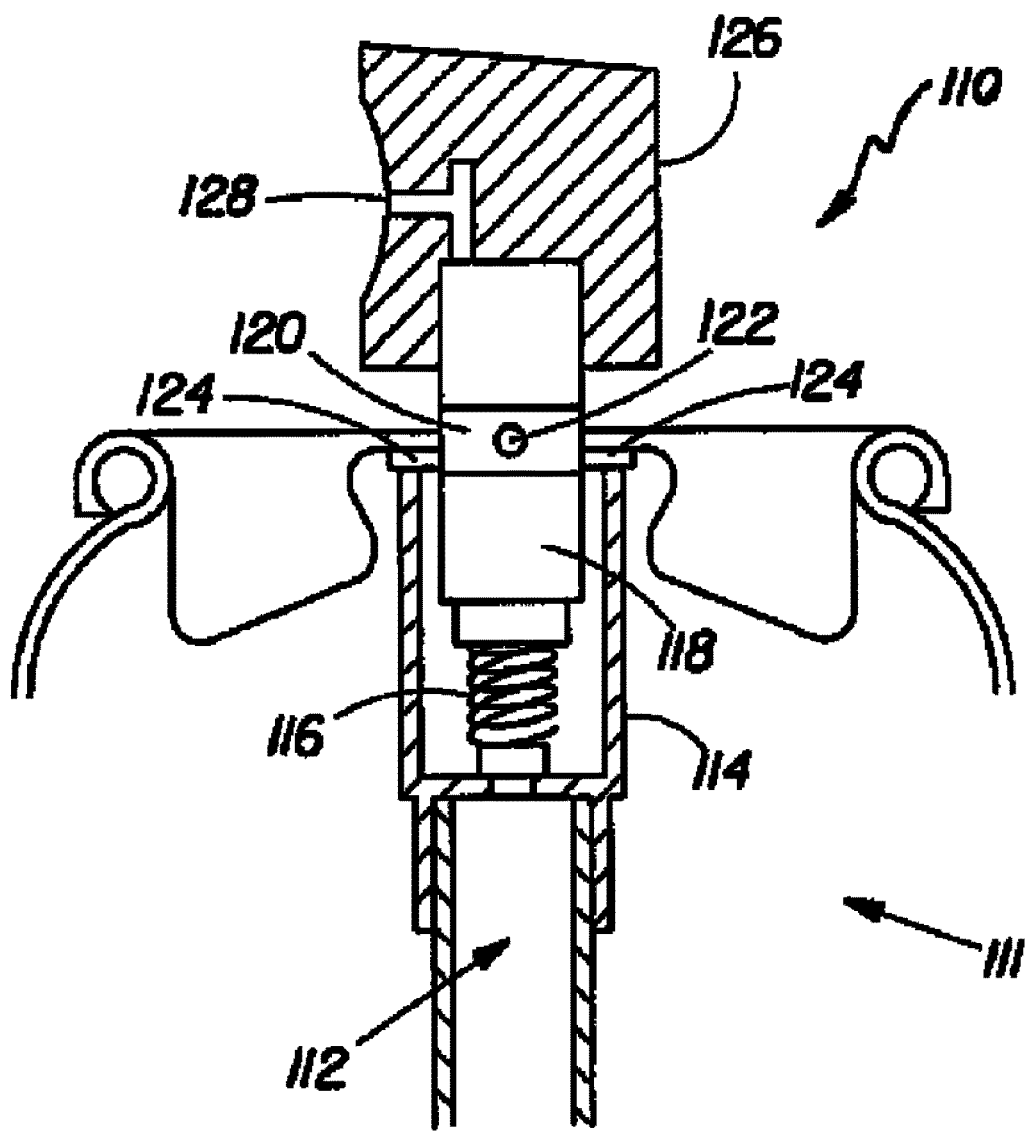
FIG. 1 depicts a side elevational view in partial section of an assembled valve mounted to a container according to one example.

As used herein, the following terms shall have the meaning specified thereafter:

"Defoamer", as used herein, is a chemical additive that reduces and hinders the formation of foam.

"Non-volatile," as it relates to at least fatty alcohols and silicones, can refer to having a boiling point at 1.0 atmospheres of about 260° C. or greater, about 275° C. or greater, or about 300° C. or greater.

"Polymer" can refer to materials formed by polymerization of one type of monomer or formed by polymerization of two or more types of monomers (i.e., copolymers).

"Thickener", as used herein, is an ingredient, typically a polymeric ingredient, used at a level sufficient to lend structure/stability to the foam system. Examples of polymeric thickeners includes, but is not limited to: Sepigel™, Simugel™ or hydrocolloids like chitosan, guar gum, and the like.

"Water soluble" can refer to being sufficiently soluble in water to form a solution that is substantially clear to a naked eye at a concentration of 0.1% in water (distilled or equivalent) at 25° C. The polymer can be sufficiently soluble to form a substantially clear solution at 0.5% concentration in water, and likely to form a substantially clear solution at 1.0% concentration in water.

II. Foam Compositions

Surprisingly, it has been found that when sebum absorbing powder, a known defoamer, is incorporated in a liquid foamable composition with a percentage of cationic surfactant and fatty alcohol, the resulting foamable composition remains stable, while providing the desired sensory and visual benefits when applied to skin. Without being bound by theory, it is thought that the combination of fatty alcohol and cationic surfactant provides a composition that easily foams and that remains stable in foam form by creating a lamellar gel network. The sebum absorbing particles provide acute visual benefits on skin by controlling shine caused by generation of sebum.

The foam composition can be formed from the combination of a liquid foamable composition with a propellant. A liquid composition is generally foamable if it has the ability to entrain or entrap gas (e.g., carbon dioxide).

In preferred embodiments, the foamable composition of the present invention exhibits a robust foam density, as well as remaining stable for a period of time after dispensation from a container, as shown in Inventive examples 1, 2 and A-H (Tables 1 and 2 below). The structural stability profile of the foam can be demonstrated by measuring the rheological storage modulus value (G') just after dispensing and about 15 minutes after dispensing. An unstable foam which has high rate of water drainage will collapse and have lower G' value after a period of time whereas a stable foam will retain its structure even after 15 min. and a comparable G' value vs. just after dispensing.

In embodiments, the foam composition has a foam density of between 0.15 g/mL, 0.2 g/mL, 0.25 g/mL to 0.3 g/mL, 0.35 g/mL, 0.4 g/mL or 0.5 g/mL, a structural stability (G' value 15 minutes after dispensation) of between 50 Pa, 100 Pa, 250 Pa or 500 Pa to 750 Pa, 1000 Pa, 1250 Pa or 1500 Pa. Furthermore, in embodiments, the foam composition has a haze value of between 20, 25, 30 or 40 to 50, 60, 70, 80 or 90.

Cationic Surfactants

Cationic surfactants suitable for use in the liquid foamable composition can include amino or quaternary ammonium moieties. Additional suitable cationic surfactants are disclosed in the following documents, all incorporated by reference herein: M.C. Publishing Co., McCutcheon's, Detergents & Emulsifiers, (North American edition 1979); Schwartz, et al., Surface Active Agents, Their Chemistry and Technology, New York, Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Suitable quaternary ammonium compounds can include those of the general formula:

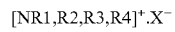

$$[NR1,R2,R3,R4]^+.X^-$$

wherein R1 to R4 can independently be an aliphatic group of from about 1 to about 22 carbon atoms or an aromatic, alkoxy, polyoxyalkylene, alkylamido, hydroxyalkyl, aryl, or alkylaryl group having from about 1 to about 22 carbon atoms; and X$^-$ can be a salt-forming anion, such as those selected from halogen (e.g., chloride, bromide, iodide), acetate, citrate, lactate, glycolate, phosphate nitrate, sulfate, and alkylsulfate radicals.

Such aliphatic groups can contain, in addition to carbon and hydrogen atoms, either linkages or other groups, such as amino groups. The longer-chain aliphatic groups (e.g., those of about 12 carbons, or higher) can be saturated or unsaturated. Mono-long alkyl quaternized ammonium salt cationic surfactants can include behenyl trimethyl ammonium salt, stearyl trimethyl ammonium salt, cetyl trimethyl ammonium salt, and hydrogenated tallow alkyl trimethyl ammonium salt. Di-long chain (e.g., di $C_{12}$-$C_{22}$, $C_{16}$-$C_{18}$, aliphatic, alkyl) and di-short chain (e.g., $C_1$-$C_3$ alkyl, $C_1$-$C_2$ alkyl) ammonium salts can also be employed. Other suitable quaternary ammonium salt useful as cationic surfactants are described in U.S. Pat. No. 8,936,798, which is hereby incorporated by reference.

Salts of primary, secondary, and tertiary fatty amines can also be suitable cationic surfactant materials. The alkyl groups of such amines can have from about 12 to about 22 carbon atoms, and may be substituted or unsubstituted. Such amines can include stearamidopropyl dimethylamine, behenylamidopropyl dimethylamine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts can include halogen, acetate, phosphate, nitrate, citrate, lactate, and alkyl sulfate salts. Such salts can include stearylamine hydrochloride, soyamine chloride, stearylamine formate, N-tallowpropane diamine dichloride, and stearamidopropyl dimethylamine citrate. Suitable cationic amine surfactants for the liquid foamable composition are disclosed in U.S. Pat. No. 4,275,055, Nachtigal, et al., issued Jun. 23, 1981, incorporated by reference herein. In certain examples, suitable cationic surfactants can include behenyl trimethyl ammonium chloride, stearyl ethylhexyldimonium methosulfate, dicetyldimonium chloride, ditallow dimethyl ammonium chloride, GENAMIN® CTAC (i.e., cetyl trimethyl ammonium chloride), esterquats (e.g., tetradecyl betainester chloride), diesterquats (e.g., dipalmitylethyl dimethyl ammonium chloride, ARMOCARE® VGH70 of Akzo, Germany), or a mixture of distearoylethyl hydroxyethylmonium methosulfate and Cetearyl Alkohol (DEHYQUART® F-75 of Henkel, Germany).

Quaternary ammonium compounds may comprise one or more of behenyl trimethyl ammonium chloride, stearamidopropyl dimethylamine, behentrimonium methosulfate ("BTMS"), behenylamidopropyl dimethylamine, stearyl ethylhexyldimonium methosulfate, dicetyldimonium chloride, and ditallow dimethyl ammonium chloride.

The foamable composition of the present invention includes from 0.05%, 0.5%, 1%, 1.5% to 3%, 3.5%, 4%, 4.5% 5% of a surfactant. In an embodiment, at least 50% and up to 100% of the surfactant is comprised of cationic surfactants. Use of cationic surfactants makes it possible to achieve a stable foamable composition at low concentrations of surfactant. Low concentrations of surfactant are preferable; as the concentration of surfactant increases, the composition becomes thicker to the point where it may eventually not foam.

Nonionic Surfactants

In an embodiment, the surfactant may include a combination of cationic and nonionic surfactants. Nonionic surfactants that may be used in combination with one or more cationic surfactants are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10-30 alkyl groups, X is —OCH$_2$CH$_2$ (i.e. derived from ethylene glycol or oxide) or —OCH$_2$CHCH$_3$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$-$C_4$ alkyl, 2-hydroxyethyl, 2-hydroxypropyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety. Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

In embodiments, the surfactant may comprise from 0%, 0.5%, 1% or 1.5% to 3%, 3.5%, 4%, 4.5% or 5% of nonionic surfactant. Furthermore, in embodiments, the ratio of cationic surfactant to nonionic surfactant may be 5:1, 4:1, 4:2 or 3:2.

Fatty Alcohols

A liquid foamable composition can include a fatty alcohol. For example, the liquid foamable composition can include monohydric saturated straight-chain fatty alcohols, such as one or more of behenyl alcohol, cetyl alcohol, and stearyl alcohol, and other waxy fatty alcohols having melting points of about 25° C. or higher, or of about 45° C. or higher; and at levels of about 10% or less, by weight of the liquid foamable composition.

In certain examples, the fatty alcohols can be non-volatile and have a low melting point. For example, such fatty alcohols can have a melting point of 30° C. or less, about 25° C. or less, or about 22° C. or less. Unsaturated fatty alcohols can also be non-volatile. Suitable fatty alcohols can include unsaturated monohydric straight-chain fatty alcohols, saturated branched-chain fatty alcohols, saturated $C_8$-$C_{12}$ straight-chain fatty alcohols, and mixtures thereof. The unsaturated straight-chain fatty alcohols can typically have one degree of unsaturation. Di- and tri-unsaturated alkenyl chains can be present at low levels; about 5% or less, by total weight of the unsaturated straight-chain fatty alcohol; about 2% or less, by total weight of the unsaturated straight-chain fatty alcohol; and about 1% or less, by total weight of the unsaturated straight-chain fatty alcohol. The unsaturated straight-chain fatty alcohols can have an aliphatic chain size of from $C_{12}$-$C_{22}$ in certain examples, from $C_{12}$-$C_{18}$ in certain examples, and from $C_{16}$-$C_{18}$ in certain examples. Exemplary alcohols of this type can include oleyl alcohol and palmitoleic alcohol.

Branched-chain alcohols can typically have aliphatic chain sizes of from $C_{12}$-$C_{22}$, $C_{14}$-$C_{20}$ in certain examples, and $C_{16}$-$C_{18}$ in certain examples. Suitable branched-chain alcohols can include isostearyl alcohol, octyl dodecanol, and octyl decanol.

Examples of saturated $C_8$-$C_{12}$ straight-chain alcohols can include octyl alcohol, caprylic alcohol, decyl alcohol, and lauryl alcohol. Fatty alcohols having a low melting point can be included at levels from about 0.1% to about 10%, by weight of the liquid foamable composition, from about 0.2% to about 5%, by weight of the liquid foamable composition in certain examples; and from about 0.5% to about 3%, by weight of the liquid foamable composition in certain examples.

It may be desirable to use waxy fatty alcohols for their conditioning benefits. However, if both waxy fatty alcohols and liquid fatty alcohols are present, a weight ratio of liquid to waxy fatty alcohols can be about 0.25 or less, in certain examples; about 0.15 or less, in certain examples; and about 0.10 or less, in certain examples.

A total amount of fatty alcohols in the liquid foamable composition can be from about 0.1%, 0.5%, 1%, 2%, 3% to 5%, 6.5%, 8% or 10%, by weight of the composition. In certain examples, a ratio of the fatty alcohol to surfactant can be about 2 parts to about 1 part. In such examples, the fatty alcohol and the cationic surfactant can combine to form liquid crystal structures in a lamellar gel phase. In examples where the ratio of the fatty alcohol to the cationic surfactant is lower (i.e., an amount of cationic surfactant is increased relative to an amount of fatty alcohol), the liquid crystal structures can be in the form of vesicles. In certain examples, the liquid crystal structures can be of any of a variety of suitable phases including, for example, bicontinuous cubic, hexagonal, inverse cubic, micellar cubic, reverse hexagonal columnar, and combinations thereof. Examples of liquid crystal structures are further described in U.S. Pat. No. 8,470,305 and PCT International Publication No. WO 2010/060131, both of which are hereby incorporated by reference.

Sebum Absorbing Powders

Sebum absorption ingredients have the capability of absorbing or removing sebum from the surface of the skin. The sebum absorbing powder may be selected from the group consisting of: porous silica, silica silylate, hydrophobically or hydrophilically surface modified silica, or a mixture thereof.

Silica is a silicone dioxide that can be modified by the addition of various chemical groups to the Si portion of silicone dioxide. Examples of Silica containing ingredients include silica silylate, silica dimethyl silylate, and silica dimethicone Silylate. Silica silylate is a hydrophobic silica derivative where some of the hydroxyl groups on the surface of the silica have been replaced by trimethylsiloxyl groups. This ingredient can be purchased under the Tradenames VM-2270 (Dow Corning, United States), Aerosil R 812 (Deggussa AG, Ger many), Aerosil RX 300 (Degussa AG, Germany), Sipemat D 17 (Degussa AG, Germany), CAB-O-SIL TS-530 (Cabot, United States), Wacker HDK H2000 (Wacker-Chemie AG, Germany). Further, silica with variable amounts of water contained therein is known as hydrated silica. This ingredient may be purchased under the Tradenames R 22S (Evonik Industries), Sipemat R 22S (Evonik Industries), Sipemat R 505 (Evonik Industries).

Another example of a sebum absorption ingredient that can be used in the context of the present invention includes silica dimethyl silylate. This ingredient is a silica derivative in which the surface of the fumed silica has been modified by the addition of dimethyl silyl groups. Silica dimethyl silylate can be purchased under the Tradenames Aerosil R 972 (Degussa AG, Germany), Aerosil R 974 (Degussa AG, Germany), Aerosil R 976 (Degussa AG, Germany), Aerosil R 976 S (Degussa AG, Germany), CAB-O-SIL TS-610 (Cabot, United States), Covasilic 15 (Sensient Cosmetic Technolo gies-LCW, France), Wacker HDK H15 (Wacker-Chemie, Germany), Wacker HDK H18 (Wacker-Chemie, Germany), and Wacker HDK $H_2O$ (Wacker-Chemie, Germany). A further example of a sebum absorption ingredient that can be used in the context of the present invention includes silica dimethicone silylate. This ingredient is a hydrophobic silica derivative in which the surface of the fumed silica has been modified by the addition of dimethicone. Silica dimethicone silylate can be purchased under the Tradename CAB O-SIL TS-720 (Cabot, United States). A further example of such a hydrophic silica is one in which the surface of the fumed silica has been modified by the addition of a cetyl moiety. This can be purchased under the Tradename Aerosil R 816 (Evonik Industries).

Other Components

The liquid foamable composition can include water in an amount such that water can provide a remainder of the liquid foamable composition.

In certain examples, the water may include other liquid, water-miscible, or water-soluble solvents such as lower alkyl alcohols (e.g., $C_1$-$C_5$ alkyl monohydric alcohols), such as $C_2$-$C_3$ alkyl alcohols. However, the liquid fatty alcohol must be miscible in an aqueous portion of the liquid foamable composition. The fatty alcohol can be naturally miscible in the aqueous portion or can be made miscible through the use of co-solvents or surfactants.

The liquid foamable composition can also include a variety of other optional components suitable for rendering such compositions more cosmetically or aesthetically acceptable or to provide them with additional usage benefits. Such conventional optional ingredients can be well-known to those skilled in the art.

For example, the liquid foamable composition can also include one or more additional conditioning agents, such as those selected from the group consisting of avocado oil, fatty acids, hexyldecanol, isopropyl myristate, lanolin, apple wax, bees wax or jojoba oil, phospholipids (e.g., lecithins or ceramides), vaseline non-volatile hydrocarbons, and hydrocarbon esters. Imidazolidinyl derivatives, such as INCI Quaternium-87 (REWOQUAT® W 575 of Witco, Germany) can also be useful.

A wide variety of additional ingredients can be included within the liquid foamable composition. Such ingredients can include other conditioning agents (e.g., betaine, carnitin esters, creatine, amino acids, peptides, proteins and vitamins); vitamin derivatives (e.g., tocophenyl actetate, niacinamide, panthenol); hair-hold polymers; detersive surfactants (e.g., anionic, nonionic, amphoteric, and zwitterionic surfactants); UV-filters (e.g., p-methoxy cinnamic acid isoamylester, lipophilic cinnamic acid esters, salicylic acid esters, 4-amino benzoic acid derivatives or hydrophilic sulfonic acid derivatives of benzophenones or 3-benzyliden campher); antioxidants (e.g., tocopheroles), preservatives (e.g., benzyl alcohol, methyl paraben, propyl paraben, and imidazolidinyl urea); polyvinyl alcohol; ethyl alcohol; pH-adjusting agents (e.g., citric acid, formic acid, glyoxylic acid, acetic acid, lactic acid, pyruvic acid, sodium citrate, succinic acid, phosphoric acid, sodium hydroxide, and sodium carbonate); salts (e.g., potassium acetate and sodium chloride); antimicrobials; humectants (e.g., sorbitol); chelators (e.g., such as those described in U.S. Pat. No. 5,487,884 issued to Bisset, et al.); sunscreens; desquamation actives (e.g., those described in U.S. Pat. Nos. 5,681,852 and 5,652,228 issued to Bisset); anti-wrinkle/anti-atrophy actives (e.g., N-acetyl derivatives, thiols, hydroxyl acids, phenol); skin soothing agents/skin healing agents (e.g., panthenoic acid derivatives, aloe vera, allantoin); skin lightening agents (e.g., kojic acid, arbutin, ascorbic acid derivatives); skin tanning agents (e.g. dihydroxyacteone); anti-acne medicaments; essential oils; sensates; coloring agents; perfumes; sequestering agents (e.g., disodium ethylenediamine tetra-acetate); and polymer plasticizing agents (e.g., glycerin, disobutyl adipate, butyl stearate, and propylene glycol). Other such suitable examples of such skin actives are described in U.S. Patent Application Publication No. 2012/0009285.

Such optional ingredients generally can be used individually at levels from about 0.01% to about 10.0%, by weight of the liquid foamable composition in certain examples; and in certain examples from about 0.05% to about 5.0% of the liquid foamable composition.

The liquid foamable composition described herein is substantially free of any thickening agents. Non-limiting classes of thickening agents include those selected from carboxylic acid polymers, crosslinked polyacrylate polymers, polyacrylamide polymers, polysaccharides, and gums.

B. Propellant

A variety of conventional propellants (e.g., gases) can be used to transform the liquid foamable composition into a foam composition. Such propellants can include carbon dioxide and nitrous oxide. In certain examples, the propellant can be only one compound, and in other examples, the propellant can be a mixture of compounds. For example, in one example, only carbon dioxide can be used as a propellant. In certain examples, the propellant can include air. Other compounds can also be included to form the propellant in amounts of up to about 1%, by weight of the total propellant. These additional propellant compounds can include propane, butane, isobutane, dimethyl ether, and $N_2O$. These additional propellant compounds can be present without causing any disadvantages. In certain examples, the foam composition can include about 20 parts of propellant per one hundred parts.

In a bag-on-valve system, for example, a propellant can be held within a container, such that the propellant surrounds an inner bag. As described herein, propellants used in a bag-on-valve system can have minimal to no interaction with a liquid foamable composition or a foam composition. As a result, types of propellant that can be used in a bag-on-valve system can be less restrictive than those used in examples where there is more interaction between the propellant and the liquid foamable composition or the foam composition. Suitable propellants for use in a bag-on-valve system can include, for example, hydrocarbons or any of a variety of suitable propellants.

In the foam composition, carbon dioxide can be included at levels of about 0.5% to about 20.0%, by weight, in certain examples; from about 1.0% to about 3.0%, by weight, in certain examples; and from about 1.5% to about 2.5%, by weight, in certain examples.

III. Aerosol Product

An aerosol product can include a liquid foamable composition, a propellant, and a package. In certain examples, the liquid foamable composition and propellant can be housed in the package, which can include a container and a valve, such that the liquid foamable composition and propellant can be combined and dispensed as a foam. In certain examples, a foam composition can be housed in a package.

The container can be any of a variety of aerosol containers or similar type containers known in the art. For example, the container can be a single chamber container or a barrier container. Non-limiting examples of single chamber containers can include plastic, glass, aluminum, or steel containers that can be unlined or lined with materials such as epoxy phenolics, organosols, and polyamide imides. In such single chamber containers, the liquid foamable composition and the propellant can be combined in the single chamber, as shown in FIG. 1. Barrier containers can keep the liquid foamable composition physically separate from the propellant within the container. Non-limiting examples of barrier containers can include a piston container and a bag-on-valve container, which are described in U.S. Patent Publication No. 2012/0288465.

The valve can be any of a variety of aerosol valves or similar type valves (e.g., any of a variety of valves supplied by APTAR®). In certain examples, the valve can be a powder valve. The powder valve can include one or more orifices on a valve stem, normally one or two orifices. Each of the orifices can have a same or different orifice diameter and can be in the form of any of a variety of shapes (e.g., circular, square, etc.). Both the orifice diameter and the orifice shape can be selected based upon the size and shape of the particulate material used in the liquid foamable composition. Further, certain valves, such as a powder valve, can help to prevent clogging of the aerosol product by wiping an opening of the orifice against a sealing gasket as the valve moves from an open position to a closed position. Non-limiting examples of suitable powder valve configurations are described in detail in U.S. Pat. Nos. 3,773,064, 5,975,378, 6,394,321 and 8,580,725.

FIG. 1 shows a portion of a container 110 to which a valve is mounted, according to one example. A valve assembly 111 can generally include a dip tube 112, a valve housing 114, a valve-closing coil spring 116, and a valve body 118. The valve body 118 can have a hollow valve stem 120 extending upwardly therefrom and can include at least one orifice 122 leading into an interior of the valve stem 120. A sealing gasket 124, which can be made of rubber or other suitable resilient material, can surround the valve stem 120 and seal the orifice 122 when the valve is in the closed position. An actuator 126 having a nozzle 128 is shown to be attached to a top of the valve stem 120. When the actuator 126 is depressed downwardly against a force of the spring 116, the valve moves to the open position, and the orifice 122 can pass below the sealing gasket 124 such that the liquid foamable composition within the container can, under the influence of the propellant, pass up through the dip tube 112, into the valve body 118, through the orifice 122, into the valve stem 120, into the actuator 126, before being dispensed out through the nozzle 128. When the actuator 126 is released, the valve can return to the closed position, such that the spring 116 can push the valve stem 120 and the orifice 122 upwardly against the sealing gasket 124, wiping any remaining liquid foamable composition away from the orifice 122 of the valve stem 120 to prevent clogging of the orifice 122 and blocking flow of the liquid foamable composition.

The actuator 126 can be any of a variety of actuators known in the art. For example, an actuator can be a front-hinged, rear-hinged, or non-hinged actuator, as long as the actuator can be properly matched with the valve stem. Non-limiting examples of suitable hinged actuators can include those available from SEAQUIST® Perfect Dispensing under the trade names S30, S25, S20, and Allegra for upright containers and S16 and S4 for inverted containers. Non-hinged actuators can be used as they can tend to exhibit less lateral pressure during actuation of the aerosol product. Non-limiting examples of suitable non-hinged actuators can include those available from Precision Valve under the trade names City Spout, Hercules Spout, and Iris and those available from SEAQUIST® Perfect Dispensing under the trade name S2. Actuators, valves, containers, and other related parts and equipment can include those available from, for example, APTAR®, Precision Valve, and Summit Packaging Systems.

Figure 2:
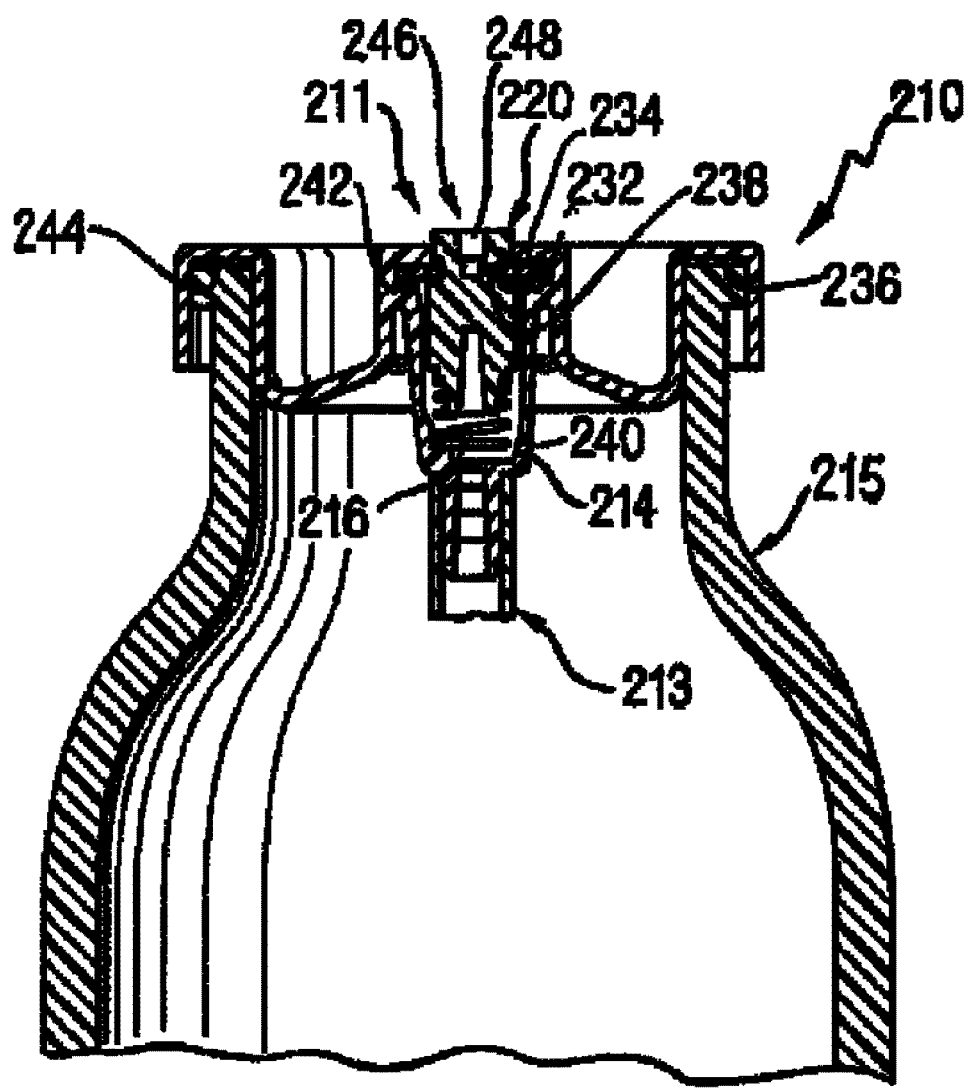
FIG. 2 depicts a schematic cross-sectional view of an inner bag housed within a container according to another example.
Figure 3:
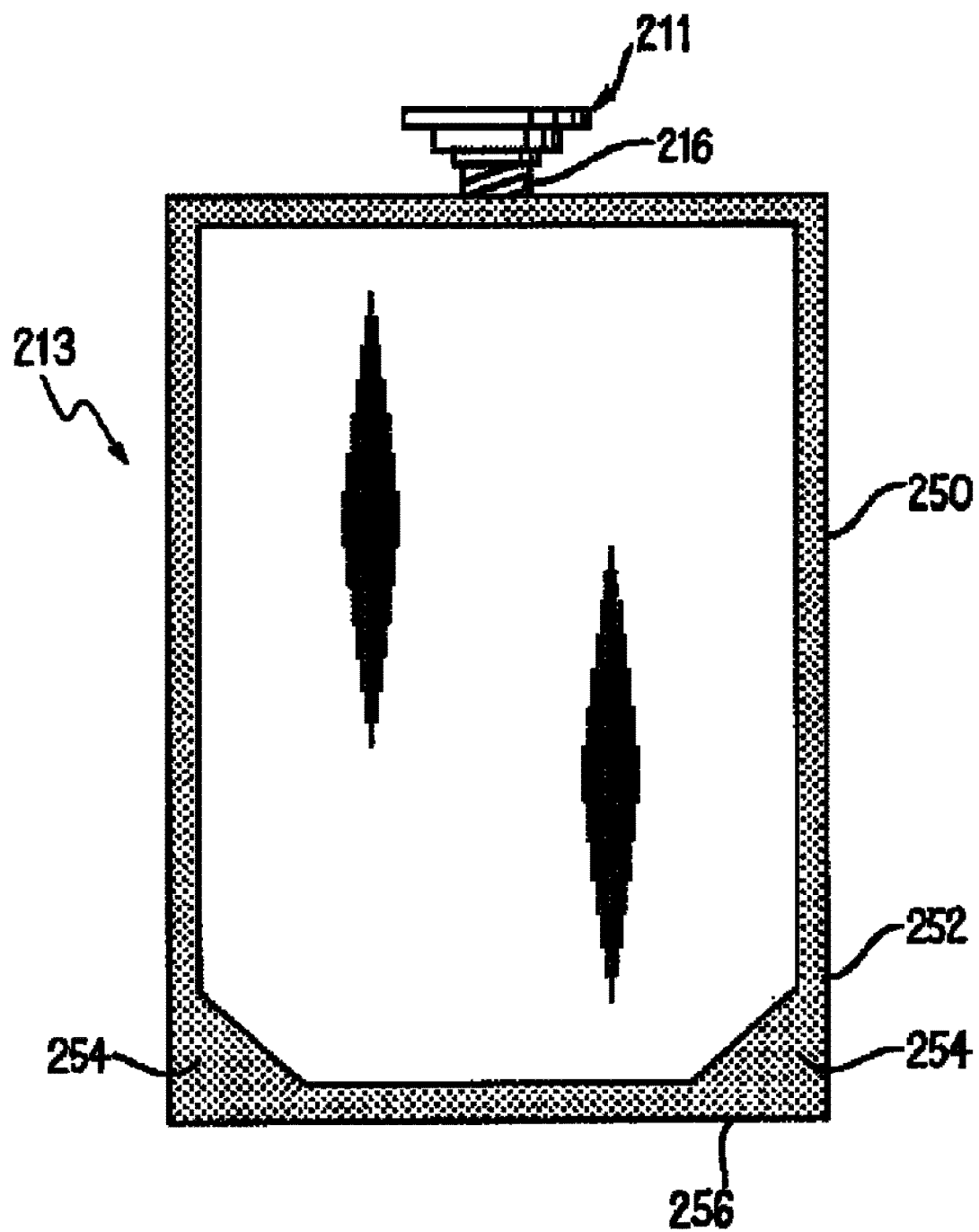
FIG. 3 depicts a front view of the inner bag of FIG. 2.

In another example, a container can include a bag-on-valve system, as mentioned herein and as shown in FIGS. 2 and 3. FIG. 2, for example, shows a bag-on-valve system including a container 210 having an inner bag 213, which can be filled with the foam composition or the liquid foamable composition, and an outer container 215, which can enclose the inner bag 213. A valve assembly 211, vertically movable between an open position and a closed position, can be attached to the inner bag 213.

The valve assembly 211 can include a housing 214, a valve stem 220, a spring 216, a valve plate 232, an inner sealing 234, and an outer sealing 236. The valve stem 220 can include one or more lateral openings 238. The spring 216 can be disposed between a lower end portion 240 of the valve stem 220 and the housing 214 and can bias the valve stem 220 upwardly towards the valve plate 232, which can be disposed at an upper end of the housing 214. The valve plate 232 can include two coaxially-arranged recesses 242, 244 extending in a circumferential direction of the valve plate 32. FIG. 2 shows an axial opening 246 located in a central portion of the inner recess 242. The inner sealing 234 can be disposed within the inner recess 242, attached to the valve plate 232, and can be adapted to engage the valve stem 220 such that the lateral opening 238 of the valve stem 220 is covered and blocked, respectively. The outer sealing 236 can be disposed in the second or outer recess 244 of the valve plate 232. The valve stem 220 can include a passage 248 in the central axial portion thereof, which can be connected to the lateral opening 238 on one side and connectable to a corresponding passage of a dispenser cap on the other side. In the closed position, a flow path from the interior space of the housing 214 along the valve stem 220 and through the lateral opening 238 can be blocked by the inner sealing 234.

The valve assembly 211 can be fixed to the inner bag 213 at an upper end thereof such that a lower end of the housing 214 of the valve assembly 211 can be gas-tight covered by the upper edge of the inner bag 213. Further, the inner bag 213 and the valve assembly 211 can be attached to the outer container 215 such that an upper end of the outer container 215 can engage the outer sealing 236 of the valve plate 232 in a gas-tight manner. Accordingly, an interior of the inner bag 213 and space between the outer container 215 and the inner bag 213 each can be independently sealed.

A dispenser cap having an actuator (not shown) can be attached to the valve plate 232 such that the actuator can engage the valve stem 220. When the actuator is depressed downwardly against a force of the spring 216, the valve assembly 211 can move to the open position. The valve stem 220 moves within the inner sealing 234, which can remain stationary, while contacting the same. Once the lateral opening 238 can be uncovered by the inner sealing 234, the flow path from the valve housing 214 through the lateral opening 238 can be opened. Thus, the interior of the inner bag 213 and the flow path inside the valve housing 214 become linked such that the foam composition/liquid foamable composition within the inner bag 213 can pass through the flow path and dispensed out of the dispenser cap by the pressure of the propellant/compressed gas, which can surround the inner bag 213.

As shown in FIG. 3, the inner bag 213 can include flat lateral edges 250 and a bottom fold 252, which can be directed towards an upper end of the inner bag 213 in order to allow a controlled collapse. Near the bottom fold 252, the inner bag 213 can include two flat triangular portions 254, each extending from the bottom edge 256 to the lateral edge 250 with an angle of about 45°. This can further facilitate the collapse of the inner bag 213, when compressed by the pressure of the propellant in the outer container 215 (as shown in FIG. 2). As described above, the outer container 215 can include any of a variety of propellants or any other suitable compressed gas. Pressure of the propellant can be set to from about 0.3 to about 1.0 MPa, or from about 0.3 to about 0.8 MPa, in order to stably discharge contents of the inner bag 213 as completely as possible.

The inner bag can be flexible, and can be made from any of a variety of suitable materials. In certain examples, the inner bag can be formed with a layer of a material that can be essentially impermeable to the propellant within the inner bag. In certain examples, the inner bag can be formed with a layer of a material that can be essentially impermeable to the propellant outside of the bag, as it may be required that such compositions do not mix during storage. Mixing of the propellant within the inner bag and the propellant outside of the bag can be inappropriate based on the properties of the foam composition/liquid foamable composition or any of a variety of other reasons. However, this does not preclude the possibility that the propellant within the inner bag and the propellant outside of the bag can be mixed upon dispensing of the foam composition/liquid foamable composition when a valve to dispense the foam is triggered. For example, a mixing channel (not shown) or another appropriate measure can be used in such a case to mix the respective propellants if desired.

IV. Method of Use

The foam composition can be used in conventional ways to improve sensory benefits and impart acute look benefits to skin. This generally involves application of an effective amount of the foam composition to a portion of the skin of a user. For example, the foam composition can be dispensed from an aerosol can or similar container or package, and the foam composition can be applied and rubbed onto a desired portion of the skin of a user. An "effective amount" can refer to an amount sufficient enough to provide the desired sensory benefits, which can include, for example, a rich and creamy appearance and a favorable "feel" along with acute appearance benefits.

In certain embodiments, the foam composition can provide the rich and creamy appearance and moisturization and protection capabilities associated with heavier products, while providing a rapid absorption and ease of application associated with lighter products. Furthermore, the foam composition can reduce or eliminate characteristics associated with a negative sensory experience such as, for example, tack, drag, and stickiness.

V. Procedures

A. Foam Density Determination

From a pressurized dispenser containing the foam composition, dispense enough foam into a small cylindrical cup-like container of known volume (or dimensions) and weight, such that the foam composition can rise above a rim of the cup-like container. Using a tool with a straight edge, such as a spatula, scrape off any excess foam by sweeping an edge of the spatula across the rim of the cup-like container to leave a flat smooth surface at level with a top of the cup-like container. Weigh the foam composition and the container, and calculate a foam density using the following formula:

$$\text{foam density} = \frac{\text{weight of cup with foam } (g) - \text{weight of empty cup } (g)}{\text{Volume of Cup (mL)}}$$

Assuming the cup-like container is cylindrical, the volume of the container can be calculated by measuring its diameter and depth with, for example, a caliper or similar measuring tool. The volume can then be calculated using the following formula:

$$\text{Volume} = (\pi) \times (\text{cup height [mm]}) \times \left(\frac{\text{cup diameter [mm]}}{2}\right)^2$$

B. Foam Stability measurement

The structural stability of the foam is assessed by measuring the rheological G' value (Storage modulus) after dispensing and re-measuring the value 15 min after dispensing. The term "G'," as used herein, refers an elastic (storage) modulus which is a measure of the amount of energy stored and retrieved when strain is applied to a composition.

The measurement was carried out on a commercially available Discovery HR 2 TM Rheometer (TA instruments) with an aluminum geometry. From a dispenser containing the foam composition, dispense enough foam into a container. Using a spatula, place 2 g of product on the plate. The geometry used for the analysis was 40 mm, 2.004° cone plate, Peltier Aluminium plate-109445. An Oscillation amplitude stress sweep is conducted for the sample from 0.1 Pa to 500 Pa at a frequency of 1 Hertz and at a temperature of 25 degree Celsius. The same measurement is repeated for the sample 15 minutes after dispensing. The G' values are reported corresponding to an oscillation strain value of 1%.

A smaller decrease in the G' value signifies a structurally stable foam. A higher G' value or small decrease in G' value at 15 min. vs right after dispensing is desirable.

C. Haze Meter

Haze corresponds to the percentage of light scattered relative to the total transmittance Total Luminous Transmittance (Tt), Diffuse Luminous Transmittance (Td), and Haze value {(Td/Tt)×I00} can be measured and calculated by the artisan by reference to ASTM D 1003-00 "Standard Test Method for Haze and Luminous Transmittance of Transparent Plastics". Although the pigments herein are not plastics, the same principles of this specific standard test can be applied. Without being bound by theory, it is believed that, by having such high Haze value, the contrast between lighted area of the skin and shaded area of the skin (such as pores and wrinkles) is minimized for reducing the appearance of the trouble areas.

D. Stickiness Measurement

The stickiness assessment was carried out on a 5 point scale by a 4 member panel. A score of 1 was assigned for low stickiness and higher values were assigned for higher perceived stickiness. The reported values are the average rating scores provided by the panelists.

VI. Examples

A. Inventive Example

Each of the inventive examples can be prepared by combining the water, surfactant, and fatty alcohol and heating the mixture to about 80° C. Liquid crystal structures (e.g., a lamellar gel structure) can be formed as the quaternary ammonium compound and the fatty alcohol combine to emulsify, stabilize, and thicken the water phase.

Table 1 shows a comparison between inventive samples (1 and 2), each using a cationic surfactant or combination of cationic surfactant and non-ionic surfactant and comparative examples 1, 2 and 3. Comparative example 1 uses a low level of only non-ionic surfactant, comparative example 2 uses a high level of only non-ionic surfactant and comparative example 3 uses a polymer together with a nonionic surfactant.

TABLE 1

|  | I1 | I2 | C1 | C2 | C3 |
|---|---|---|---|---|---|
| Water | 64.70 | 64.70 | 64.70 | 64.00 | 64.20 |
| Cetyl Alcohol (Fatty Alcohol) | 0.50 | 0.50 | 0.50 | 0.50 | 0.50 |
| Stearyl Alcohol ((Fatty Alcohol) | 1.50 | 1.50 | 1.50 | 1.50 | 1.50 |
| Glycerin (Humectant) | 2.00 | 2.00 | 2.00 | 2.00 | 2.00 |
| Dimethicone 50 cst (Wetting agent) | 20.00 | 20.00 | 20.00 | 20.00 | 20.00 |
| Propylene Glycol (Wetting agent) | 10.00 | 10.00 | 10.00 | 10.00 | 10.00 |
| Rheodol TWL-120 (Non-ionic emulsifier) | x | 0.15 | 0.30 | 1.00 | 0.30 |
| Genamin BTMS (cationic emulsifier) | 0.30 | 0.15 | x | x | x |
| Simulgel EG (Polymeric thickener) | x | x | x | x | 0.50 |
| VM 2270 Aerogel Silica (Sebum absorbing powder) | 1.00 | 1.00 | 1.00 | 1.00 | 1.00 |
| Propellant | $CO_2$ | $CO_2$ | $CO_2$ | $CO_2$ | $CO_2$ |
| Foam richness (density) | 0.17 | 0.15 | 0.083 | System is too thick to be foamable | 0.11 |
| Foam structure immediately after dispensing (rheology, G' at 1% oscillation strain) | 203.571 | 115.899 | Not applicable as foam collapsed | | 114.625 |
| Foam structure data 15 min after dispensing (rheology, G' at 1% oscillation strain) | 276.115 | 170.995 | Not applicable as foam collapsed | | Not applicable as foam collapsed |
| Stickiness 5 min after application (on a scale of 1-5, n = 4) | 1.25 | 2 | 1.75 | | 4.25 |

As can be seen in comparative example 3, where a polymer (Simugel EG) is used in combination with a sebum absorbing powder (VM 2270 Aerogel Silica), the density of the foam (richness) is below the threshold value required to provide the sensory benefit of the present invention. Furthermore, although the "foam" has some structure immediately upon dispensation, 15 minutes post dispensation the foam has collapsed without structure, and even 5 minutes after dispensation, it has an unacceptable stick/tacky feel.

Comparative examples 1 and 2 show measurements when only a non-ionic surfactant is used. It can be seen from comparative example 1 that uses a lower concentration of surfacant that although a foam is dispensed, it collapses immediately. To note, the amount of non-ionic surfactant used in comparative example 1 is the equivalent to the total amount of surfactant used in both inventive examples 1 and 2. Likewise, in comparative example 2 with a higher concentration of non-ionic surfactant, the liquid foamable composition is too thick to be foamable. By contrast, when cationic surfactant is used alone or when used in combination with a non-ionic surfactant, a foam is produced with stable rheology.

Table 2:

Table 2 shows a range of different example formulations of liquid foamable composition that meet the desired sensory and look targets. Specifically, the surfactants and fatty alcohol chemistries and concentrations are chosen such that the resulting foam composition remains liquid and foamable.

| Inventive Examples | A | B | C | D | E | F | G | H |
|---|---|---|---|---|---|---|---|---|
| Water | 74.80 | 56.65 | 29.16 | 44.22 | 33.48 | 26.51 | 36.66 | 89.10 |
| Fatty Alcohol | 2.00 | 2.72 | 1.40 | 1.88 | 1.58 | 1.09 | 1.76 | 3.00 |
| Humectant | 2.00 | 4.25 | 2.19 | 1.88 | 1.88 | 0.73 | 2.75 | 3.00 |
| Wetting agent | 19.00 | 29.00 | 60.00 | 48.00 | 50.00 | 66.67 | 50.00 | 1.75 |
| Emollient | 0.00 | 0.00 | 0.00 | 0.00 | 1.00 | 0.00 | 0.00 | 2.50 |
| Non-ionic emulsifier | 0.20 | 0.13 | 0.07 | 0.16 | 0.08 | 0.11 | 0.08 | 0.15 |
| Cationic emulsifier | 1.00 | 4.25 | 2.19 | 1.88 | 2.00 | 0.73 | 2.75 | 0.50 |
| Sebum Absorbing Powder | 1.00 | 3.00 | 5.00 | 2.00 | 10.00 | 4.17 | 6.00 | 0.10 |
| Propellant | $CO_2$ | $CO_2$ | $CO_2$ | $CO_2$ | $CO_2$ | $CO_2$ | $CO_2$ | $CO_2$ |
| Density of foam | 0.18 | 0.16 | 0.24 | 0.35 | 0.31 | 0.23 | 0.16 | 0.26 |
| G' at t = 0 (Oscillation strain = 1%) | 255.50 | 113.53 | 522.05 | 721.47 | 893.18 | 533.23 | 238.00 | 262.37 |
| G' at t = 15 Oscillation strain = 1%) | 249.89 | 67.37 | 847.16 | 777.24 | 1010.99 | 386.17 | 275.53 | 361.74 |
| G' ratio | 0.98 | 0.59 | 1.62 | 1.08 | 1.13 | 0.72 | 1.16 | 1.38 |
| Haze | 31.80 | 48.20 | 87.20 | 68.00 | 86.50 | 60.30 | 76.50 | 72.60 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The products and methods/processes of the present disclosure can comprise, consist of, and consist essentially of the essential elements and limitations of the invention described herein, as well as any of the additional or optional ingredients, components, steps, or limitations described herein.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in the document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid foamable composition comprising:
   a) 0.05% to about 5% by weight of the composition of one or more surfactants, wherein at least 50% of the one or more surfactants is a cationic surfactant;
   b) 0.1% to about 10%, by weight, of a fatty alcohol;
   c) 0.1% to 10% of a sebum absorbing powder;
   d) a mixture of surfactants, wherein the mixture of surfactants comprises a non-ionic surfactant; wherein a ratio of cationic surfactant to nonionic surfactant is 1:1 to 50:1;
   e) a propellant, wherein the foam composition is stored in a container and upon dispensing from the container, the foamable composition forms a foam that has a density of at least 0.15 g/m and a foam stability measurement of at least 50 Pa 15 minutes after being dispensed from the container; and
   wherein the composition is free of a thickening agent.

2. The liquid foamable composition of claim 1, wherein the ratio of cationic surfactant to nonionic surfactant is 3:2 to 5:1.

3. The liquid foamable composition of claim 1, wherein a ratio of fatty alcohol to surfactant is at least 2:1 to 3:5.

4. The liquid foamable composition of claim 1, wherein the sebum absorbing powder is selected from the group consisting of: silica, hydrated silica, silica silylate, hydrophobically or hydrophilically surface modified silica silylate, and mixtures thereof.

5. The liquid foamable composition of claim 1, wherein the composition is substantially free of a thickening agent.

6. The liquid foamable composition of claim 1, wherein the cationic surfactant includes an amino or quaternary ammonium moiety.

7. The liquid foamable composition of claim 1, further comprising at least one of niacinamide, panthenol, and hexyldecanol.

8. The foam composition of claim 1, wherein the foam composition has a haze value of greater than 20.

* * * * *